(12) United States Patent
Norton et al.

(10) Patent No.: US 9,820,771 B2
(45) Date of Patent: Nov. 21, 2017

(54) APPARATUS AND METHOD FOR MINIMALLY INVASIVE SURGERY

(75) Inventors: Michael J. Norton, Tyler, TX (US); Noel D. Ischy, Tyler, TX (US)

(73) Assignee: Axcess Instruments Inc., Tyler, TX (US)

(*) Notice: Subject to any disclaimer, the term of this patent is extended or adjusted under 35 U.S.C. 154(b) by 2311 days.

(21) Appl. No.: 11/710,388

(22) Filed: Feb. 23, 2007

(65) Prior Publication Data
US 2007/0208312 A1 Sep. 6, 2007

Related U.S. Application Data

(60) Provisional application No. 60/779,136, filed on Mar. 3, 2006.

(51) Int. Cl.
*A61B 17/34* (2006.01)

(52) U.S. Cl.
CPC ...... *A61B 17/3421* (2013.01); *A61B 17/3474* (2013.01); *A61B 2017/3419* (2013.01); *A61B 2017/3445* (2013.01); *A61B 2017/3447* (2013.01); *A61B 2017/3492* (2013.01)

(58) Field of Classification Search
CPC ........ A61B 17/3421; A61B 2017/3492; A61B 2017/3447; A61B 2017/3445; A61B 2017/3425; A61B 2017/00278; A61B 17/3423; A61B 17/3431; A61B 17/3474; A61B 2017/3419; A61B 2017/3484
USPC ......... 606/108, 185; 604/173–175, 539, 284, 604/93.01, 264, 103.04, 164.01, 167.01, 604/164.04; 600/114, 115, 201–208, 184
See application file for complete search history.

(56) References Cited

U.S. PATENT DOCUMENTS

| | | | |
|---|---|---|---|
| 4,016,884 A * | 4/1977 | Kwan-Gett | 604/175 |
| 4,306,545 A * | 12/1981 | Ivan et al. | 128/887 |
| 4,402,683 A * | 9/1983 | Kopman | 604/175 |
| 5,183,471 A | 2/1993 | Wilk | |
| 5,269,772 A | 12/1993 | Wilk | |
| 5,507,758 A | 4/1996 | Thomason et al. | |
| 6,066,090 A | 5/2000 | Yoon | |
| 6,086,603 A | 7/2000 | Termin et al. | |
| 6,277,064 B1 | 8/2001 | Yoon | |
| 6,440,061 B1 | 8/2002 | Wenner et al. | |
| 6,454,783 B1 * | 9/2002 | Piskun | 606/185 |
| 6,551,270 B1 | 4/2003 | Bimbo et al. | |
| 6,648,816 B2 | 11/2003 | Irion et al. | |
| 6,669,674 B1 * | 12/2003 | Macoviak et al. | 604/264 |
| 2005/0137609 A1 * | 6/2005 | Guiraudon | 606/108 |
| 2005/0251144 A1 * | 11/2005 | Wilson et al. | 606/73 |
| 2006/0020241 A1 * | 1/2006 | Piskun et al. | 604/93.01 |
| 2007/0049966 A1 * | 3/2007 | Bonadio et al. | 606/206 |

* cited by examiner

*Primary Examiner* — Katrina Stransky
(74) *Attorney, Agent, or Firm* — Locke Lord LLP; Scott D. Wofsy; Arpita G. Buesing

(57) ABSTRACT

A single body port or body flange access device and method for performing laparoscopic surgery are disclosed. The device comprises a plurality of crisscrossing conduits through which surgical instruments may be inserted. The instruments are manipulated so that triangulation is obtained using one patient body flange while standard surgical procedures are performed on the patient.

14 Claims, 10 Drawing Sheets

PRIOR ART

Figure 18A
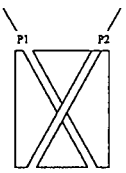
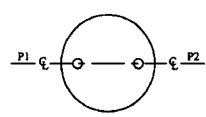
Figure 18B
Figure 19A
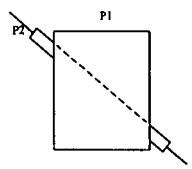
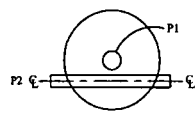
Figure 19B
Figure 20A
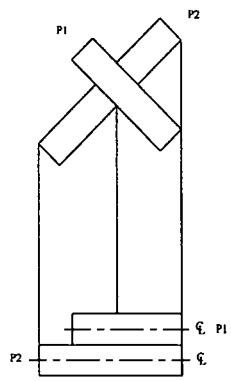
Figure 20B

APPARATUS AND METHOD FOR MINIMALLY INVASIVE SURGERY

This application claims the benefit of priority of U.S. Provisional Application Ser. No. 60/779,136, filed on Mar. 3, 2006.

TECHNICAL FIELD OF THE INVENTION

This device and method relate to laparoscopic surgical procedures and in particular to an improved device and method for minimally invasive surgical procedures.

BACKGROUND OF THE INVENTION

Minimally invasive surgery has improved patient care by decreasing pain, shortening hospital stays, offering a faster recovery time and much smaller scars. In fact the surgical procedure is much shorter than standard procedures and offers less chance of infection, etc. These laparoscopic procedures are proving popular with the patient.

During minimally invasive procedures for the abdominal surgeries such as:
 laparoscopic appendectomy (removal of the appendix);
 laparoscopic cholecystectomy (removal of the gallbladder);
 laparoscopic colectomy (removal of part or all of the colon);
 laparoscopic fundoplication (corrects severe or persistent acid reflux);
 laparoscopic hysterectomy (removal of the uterus); or
 laparoscopic ventral hernia repair (repair of an abnormal bulging of the abdominal wall often at the site of a previous surgical incision),
the surgeon makes a series of three to five small, dime-sized incisions in the patient's abdomen. Carbon dioxide gas is used to inflate the abdomen and create a working space between the internal organs and the skin. A small video camera, or scope, then is placed in one of the incisions, providing the surgeon with a magnified view of the patient's internal organs on a television monitor in the operating room. In some procedures, like MIP for colon conditions, a slightly larger incision may be needed.

Thus, the procedure requires body access devices, which are utilized to introduce visualization equipment and operative instruments rather than a standard incision to access a required part of the body. Nonparallel instrumentation is necessary to create a "depth of field" (3-dimensional vision) and introduce a variety of instrumentation. This concept is commonly known as triangulation.

In past multichannel devices have been used by the surgeon using narrow parallel channels (within the single multichannel access device). These narrow parallel channels have been found to limit the field of view and reduce depth perception. Thus, multichannel devices have not met the needs of the surgical community and are rarely used.

Nonparallel multiple access devices would allow the surgeon to introduce numerous types of instruments with triangulation through one body access opening. This concept would preserve triangulation and create the required field and depth of view while allowing the surgeon to utilize one body flange for multiple simultaneous tasks, which would be required to complete an operation on any applicable body area or space.

The current state of the art utilizes entry devices (body flanges) that have a similar cross-section as a silver dollar and incorporate a control head (gas in fusion port and sealing systems for insertable surgical instruments that have almost double cross-section as the part of the flange that attaches to the abdominal wall or body entry port. This means that large incisions will be used when operating on obese patients to allow for the large control head.

Wilk in U.S. Pat. No. 5,183,471 discloses a "Laparoscopic Cannula" that has a central conduit with a side crossing conduit that passes through the central conduit thereby creating an obstacle within the central conduit. The disclosure teaches a means to facilitate the temporary insertion of an extra laparoscopic instrument without having to make another perforation of the abdomen. The side crossing conduit will require that the central conduit be large; otherwise, a standard instrument would not be able to pass through the central conduit. The central conduit will allow a surgical instrument to "look" vertically downward over the operation point while the side crossing conduit will pass an instrument to one side of the operation point. Wilk continues to teach a second body flange for illumination and vision and does not discuss triangulation.

Wilk in U.S. Pat. No. 5,269,772 discloses a "Laparoscopic Cannula Assembly and Associated Method" which essentially is two parallel swiveling conduit passing through the same body opening and is a continuation-in-part of his '471 disclosure examined above. The parallel conduits do not cross over each other; however, the device will allow one instrument to be to one side of the operation point while the other instrument may be to the other side. The swiveling assembly will require a rather large opening in the abdomen wall. As in his '471 disclosure, he continues to teach a second body flange for illumination and vision and does not discuss triangulation.

Yoon in U.S. Pat. No. 6,066,090 discloses a "Branched Endoscope System" which discusses a single body flange having a plurality of tubes passing through the conduit for various surgical instruments. Yoon shows an embodiment in which the inside section of the body flange splits in two parts each having a bend thereby allowing a tube to overlook the other tube. The Yoon '090 device is designed to pass through the current art body flange having a single conduit.

Yoon in U.S. Pat. No. 6,277,064 discloses a "Surgical Instrument with Rotatably Mounted Offset Endoscope." The apparatus is a variation of the '090 device and is designed to pass through the current art body flange having a single conduit.

Wenner et al. in U.S. Pat. No. 6,440,061 disclose a "Laparoscopic Instrument System for Real-Time Biliary Exploration and Stone Removal." This device has multiple ports within its system, but, like Yoon, is designed to pass through the current art body flange having a single conduit.

Bimbo et al. in U.S. Pat. No. 6,551,270 disclose a "Dual Lumen Access Port." The device is essentially a current state of the art body flange with parallel entry ports that open into a single conduit which will accept two surgical tools through one body flange without ensuring a three dimensional field of view. Bimbo teaches multiple instruments through a single conduit but does not explore the concept of a single body flange replacing surgical procedures using multiple body flanges.

Thus, what is needed in the art is an apparatus and method that would allow the surgeon to perform minimally invasive operations with body flanges having a smaller overall cross-section while allowing for triangulation within the patient. Such a device and method will result in with fewer incisions for body access openings thus further decreasing the pain caused by surgery and further decreasing the recovery time and further reducing the risk of infection.

SUMMARY OF THE INVENTION

The invention consists of a "body flange" or "trans-axis-uniport" ("TAU") which is anchored to the body with a standard suture anchoring points. In turn, the body anchor contains a crisscrossed plurality of conduits which allow nonparallel introduction of equipment and/or instruments. The conduits may be parallel, nonparallel, straight or curved, but enter the body through one body opening. (It may be necessary during some procedures to have additional body openings.)

BRIEF DESCRIPTION OF THE DRAWINGS

FIG. 18A is a diagrammatic cross-sectional view of the instant inventions showing how the apertures "crisscross" within the body anchor.

FIG. 18B is a diagrammatic top view of the instant device showing how the crisscrossed apertures align the surgical instruments so that triangulation is readily obtained.

FIG. 19A is a diagrammatic cross-sectional view of a first example of the prior art of Wilk.

FIG. 19B is diagrammatic top view of the first example of the prior art showing how the surgical instruments are offset.

FIG. 20A is a diagrammatic cross-sectional view of a second example of the prior art of Wilk.

FIG. 20B is diagrammatic top view of the second example of the prior art showing how the surgical instruments are offset.

DESCRIPTION OF THE PREFERRED EMBODIMENT

In reading this disclosure, the reader should understand that the term body flange generally means the entire device used to temporarily seal an incision in a patient. Thus, the body flange would include the body anchor—the section of the device that fits within the abdominal wall and is temporality sutured to the abdominal lining, any passageways extending through the body anchor (both above and below), any seals or other apparatus that is required to form the complete temporary entry closure.

Figure 6:
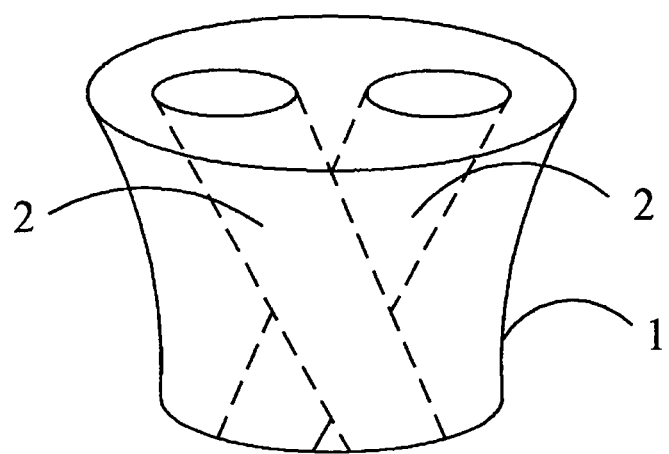
FIG. 6 shows the body anchor of the instant invention showing how the conduit apertures cross over within the anchor.
Figure 14:
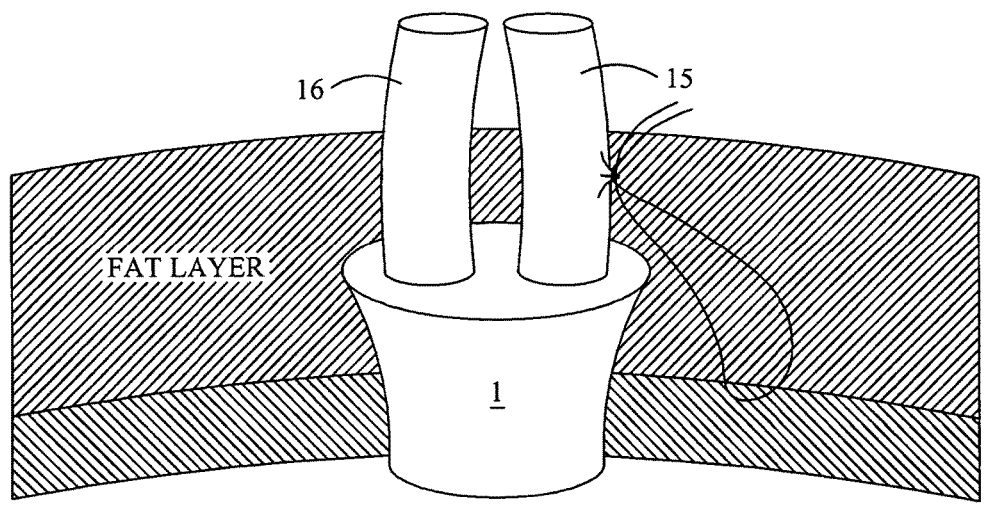
FIG. 14 shows the dual bent conduit embodiment of the instant invention as utilized in an obese patient. Note the small cross-section afforded by the bent conduit structure.

Refer now to FIG. 6 which shows an oblique view of the body anchor, 1, of the instant invention. The invention comprises of two crisscrossed (non-parallel) apertures, 2 and 3, passing through the body anchor. FIG. 14 shows an alternate embodiment in which two parallel apertures, 5 and 6, pass through the body anchor, 1. Not shown are the standard suture anchor points or tiedowns on the anchor.

Figure 1:
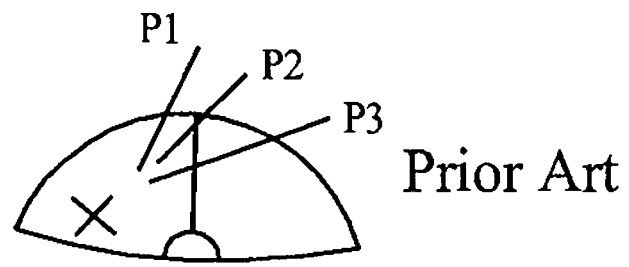
FIGS. 1 and 2 show the body access openings required for a laparoscopic appendectomy as practiced in the current art.
Figure 4:
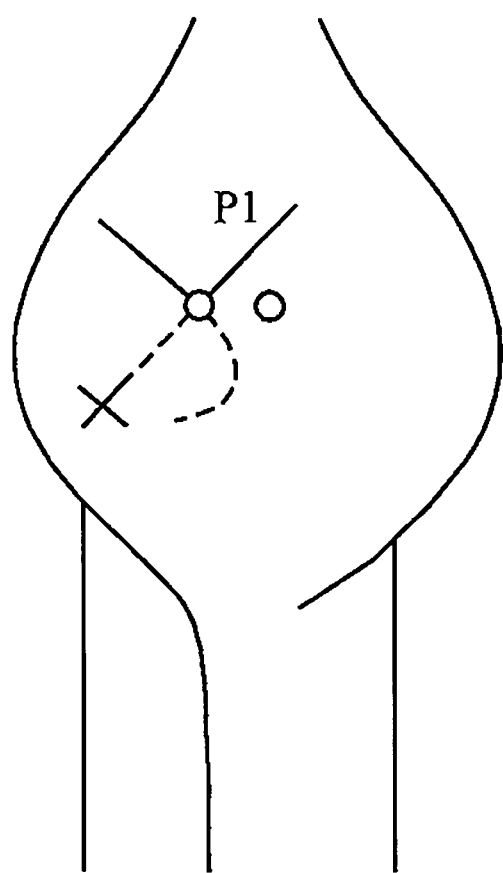
Figure 5:
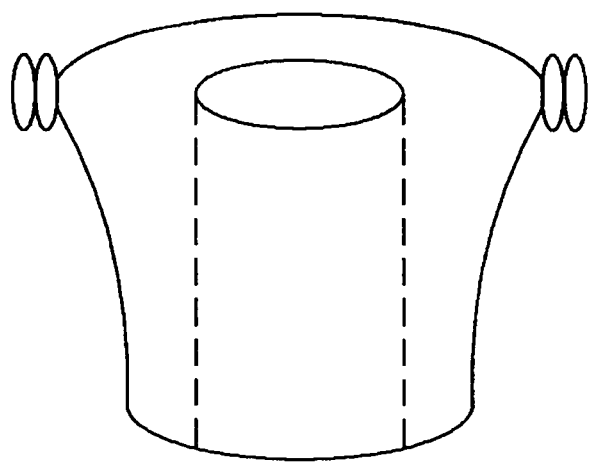
FIG. 5 shows a close up view of the current state of the art body anchor.
Figure 7:
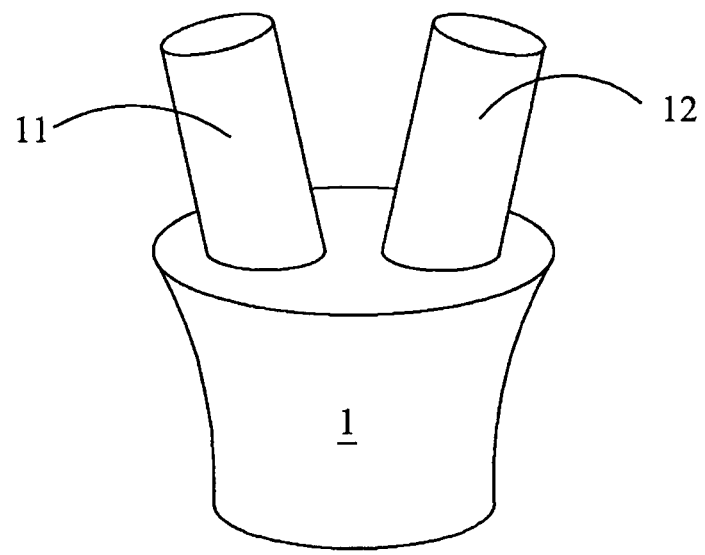
FIG. 7 shows a dual straight conduit embodiment of the instant invention.

FIG. 7 shows the complete body flange utilizing the straight instrument conduit, 11 and 12, embodiment. Not shown are required seals within the conduits, which are similar to the current art and serve to retain the body inflation gas while various instruments are inserted and withdrawn through the body flange during the operation. Such a representative seal is shown in FIG. 4 of U.S. Pat. No. 6,551,270, which is incorporated by reference. Similarly the standard inflation gas port(s) is not shown. A representative gas port is shown in FIG. 1 of U.S. Pat. No. 6,440,061 which is incorporated by reference. The '061 patent also discusses gas seals.

Figure 8:
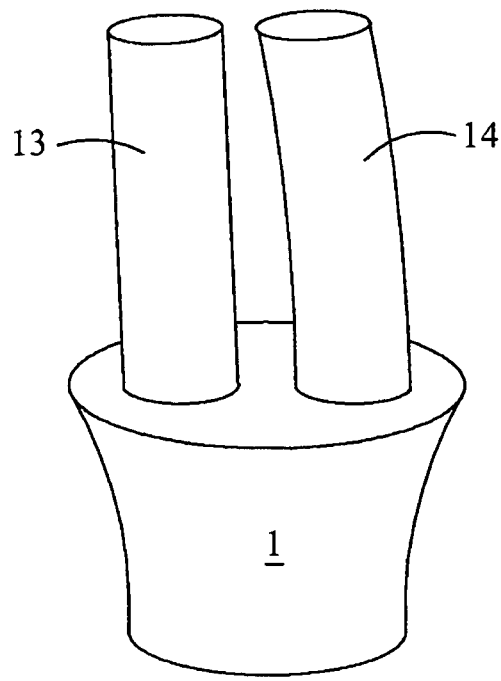
FIG. 8 shows a dual conduit embodiment of the instant invention having one straight conduit and one curved conduit.
Figure 9:
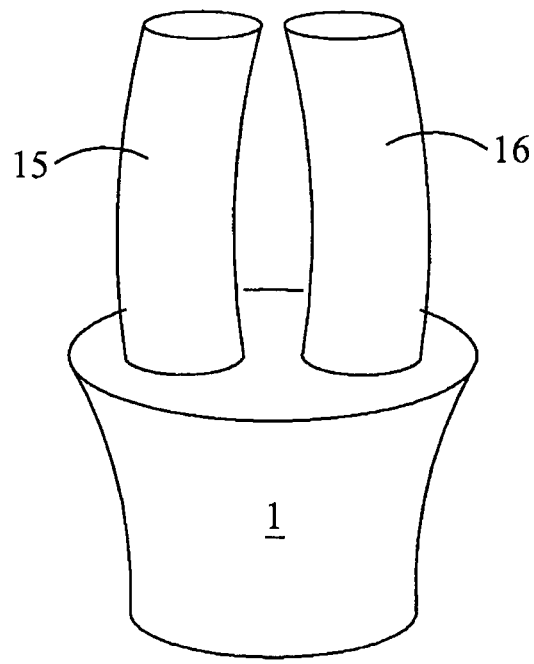
FIG. 9 shows a dual curved conduit embodiment of the instant invention.

FIG. 8 shows an alternate embodiment of the instant invention utilizing one straight conduit, 13, and a curved or bent conduit, 14. FIG. 9 shows a further embodiment of the instant invention utilizing two curved conduits, 15 and 16.

Figure 15:
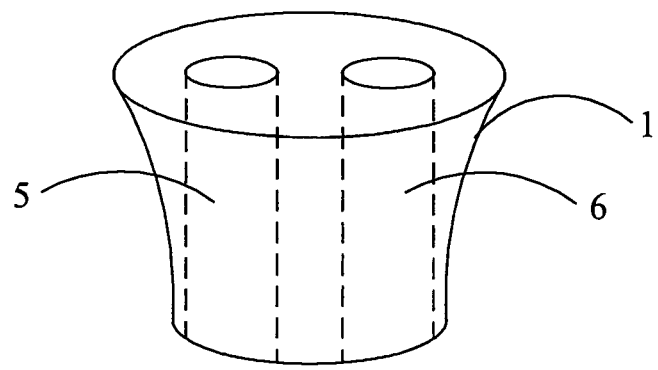
FIG. 15 shows the parallel aperture embodiment of the instant invention.

FIGS. 3 and 4 and FIGS. 6 through 14 and FIG. 16, detail the crisscrossed nature of the longitudinal axis of each conduit passing through crisscrossed apertures within the body flange. This is the preferred invention because the preferred mode allows for ready triangulation of instrumentation (as explained below). It is possible to obtain triangulation with parallel apertures as shown in FIG. 15 and thus parallel apertures (with guiding conduit) are considered within the scope of the instant invention.

Figure 3:
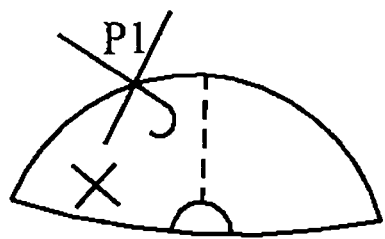
FIGS. 3 and 4 show the body access opening required for a laparoscopic appendectomy as practiced in the instant invention. Note how the two ports (which may be multiple) cross each other providing a field of view.
Figure 13:
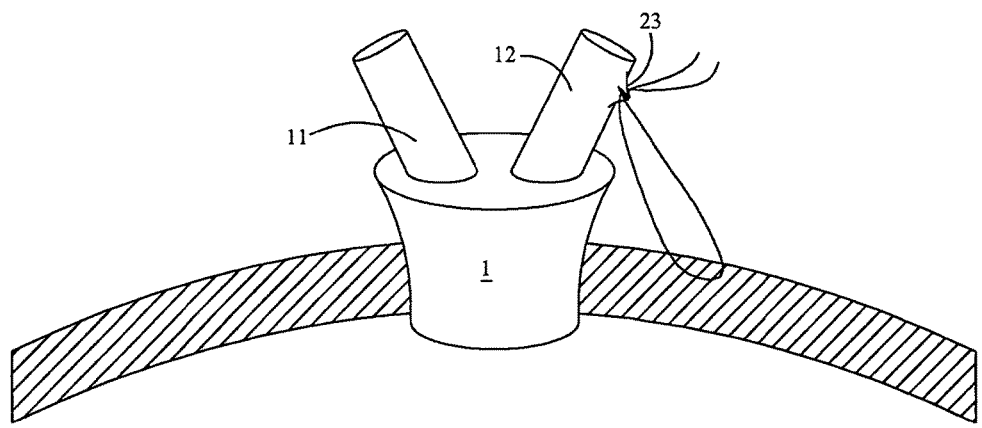
FIG. 13 shows the instant invention embedded in the abdomen wall illustrating a suture tiedown passing into the abdomen wall and returning to the suture tiedown point incorporated into the outside wall of a conduit.

FIGS. 13 and 14 show cross-sectional views through the body of the instant device used in the illustration of FIGS. 3 and 4. FIG. 13 shows the embodiment of FIGS. 7 and 12 (both conduit being straight) used in a normal person. A single suture is shown running through the abdominal lining and passed back up to the notch, 22: this suture holds the body flange, 1, in place during the operation. The second required suture is not shown (for clarity) but will also terminate in the notch. The technique is similar to the current state of the art. (It is possible to manufacture a system having a second notch—not shown—on the other conduit.)

Figure 10:
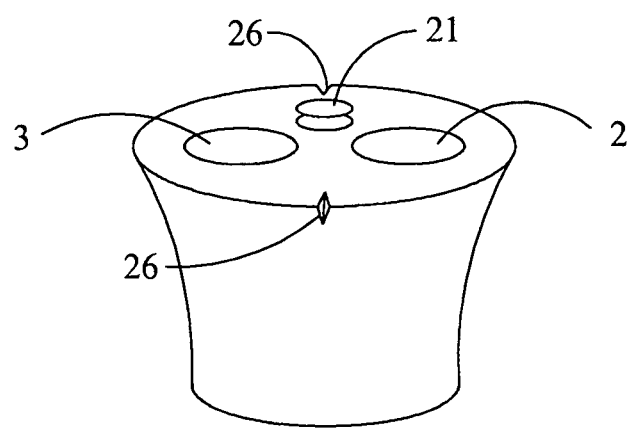
FIG. 10 shows the body anchor of the instant invention illustrating a standard suture tiedown.
Figure 11:
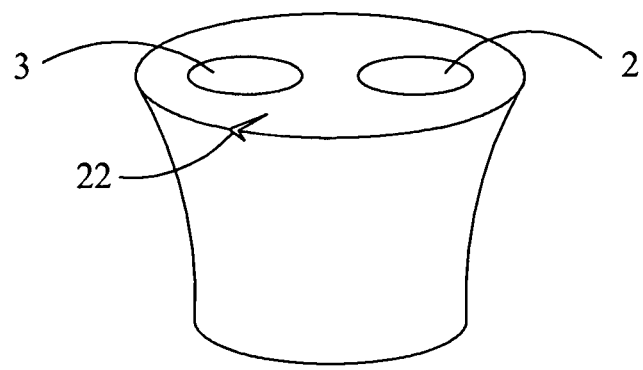
FIG. 11 shows the body anchor of the instant invention illustrating one form of a v-notch suture tiedown.
Figure 12:
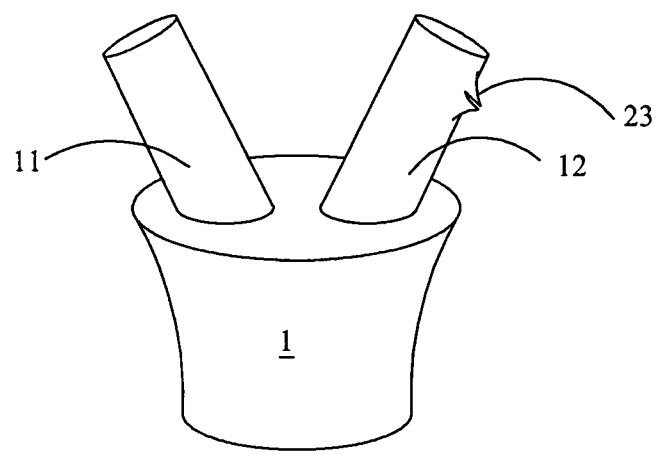
FIG. 12 shows the instant invention with the v-notch suture tiedown incorporated in one of the conduit outside walls.

FIG. 10 shows an alternate suture "tie post" or tie-off, 21, based on the prior art. Because the body anchor is so small only one post is required, but the suture requires a guide, 26, to stop the two sutures from sliding around the circumference of the plug.

FIG. 14 shows the noticeable advantage of the instant device when used in obese persons. FIG. 14 shows the embodiment of FIG. 9 in which both conduits are curved. The crisscross occurs within the body flange itself, but because the curved conduits, 15 and 16, pass over and beside each other on the outside (of the flange) the resulting cross-section remains the same as the cross-section of the body flange or at worst only slightly larger. Thus, the incision size is substantially reduced over the current art. Again, a suture is run through the abdominal lining and passed back up to the notch, 24: this suture holds the body flange, 1, in place during the operation. (Only one of two sutures is shown for clarity.) Note that an anchor using the suture post of FIG. 10 may be substituted for the notches, 23 and 24.

Figure 16:
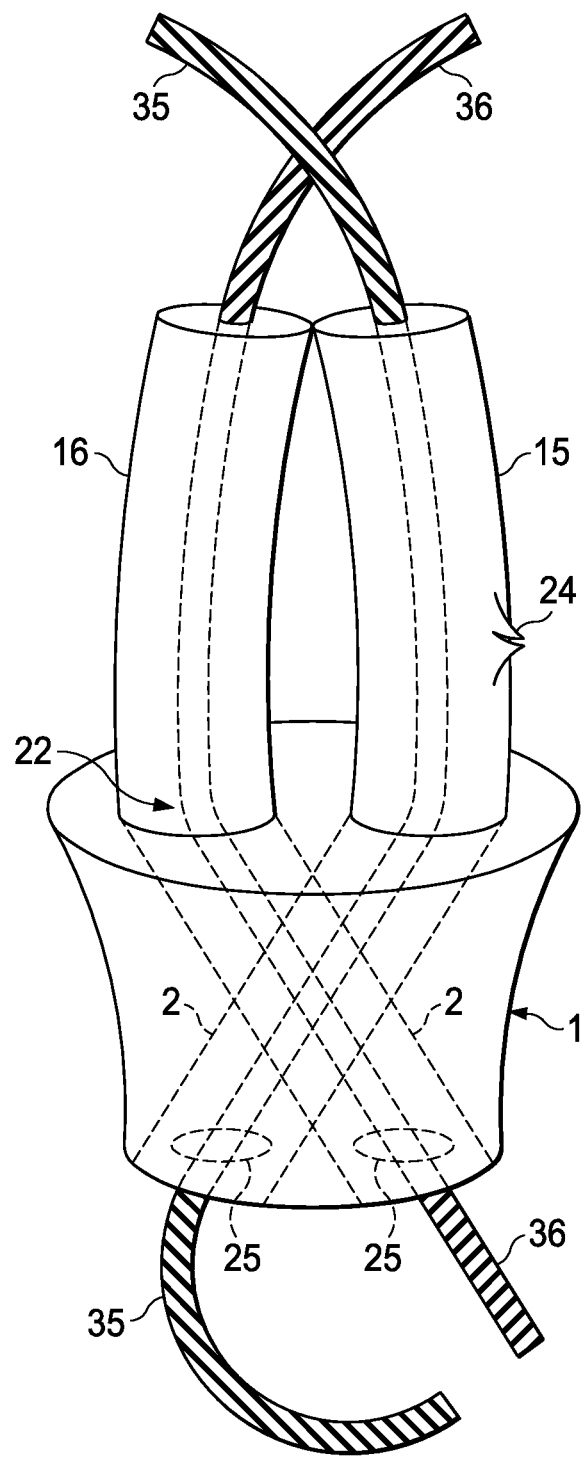
FIG. 16 shows how the dual curved conduit embodiment of the instant invention with surgical instruments clearly illustrating the three dimensional triangulation obtained through the instant invention.

FIG. 16 shows the instant device in use with surgical instruments. The straight instrument, 36, represents a standard instrument and the bent instrument, 35, simulates a flex scope with a bend. The bend serves only to illustrate how the surgical instruments function together: while still being independent. For simplicity the term instrument is used to designate the actual medical (surgical) instrument that is passing through the conduits of the body flange of the instant invention. The term flex-scope is the standard adjustable video scope used in surgical procedures. FIG. 16 shows suture notches, 22 and 24. This is for the purposes of illustration only as only one such notch is required; furthermore the tie post, 21, and guides, 26 of FIG. 10 may be substituted.

The size of the flex-scope can vary and is set by the number of instrument channels within the flex-scope. The important and key instrument is the bendable flex-scope shown in the figure cross coupled with a standard instrument (or flexible instrument) so that a three dimensional view is obtained and maintained during the procedure. The "bendable" channel houses the optics used in the laparoscopic procedure (camera and illumination). Note that due to the bendable channel the optics will provide a field of view that approaches that of a three dimensional view of the surgical area.

Figure 17A:
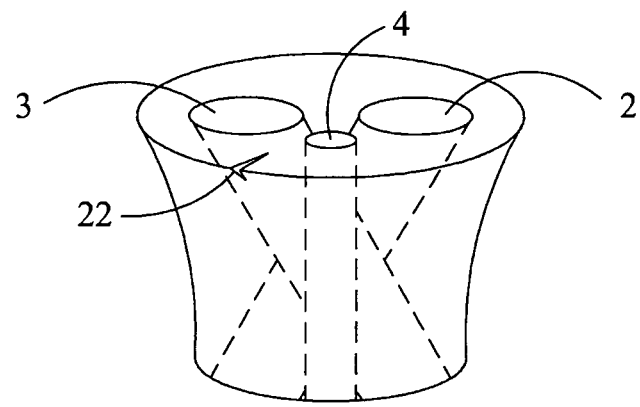
FIG. 17A shows an alternate embodiment of the body anchor having crisscrossed apertures with a central straight aperture.

FIG. 17A is a further embodiment of the body anchor showing the crisscrossed apertures along with a third aperture, 4, that will place a surgical instrument midway inline with the instruments using the other apertures, 2 and 3.

Figure 17B:
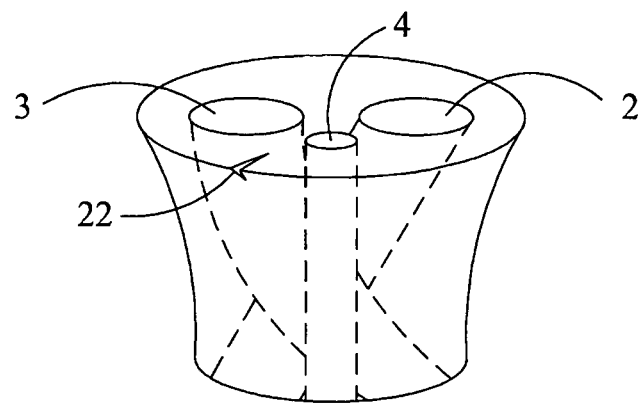
FIG. 17B shows an alternate embodiment of the body anchor having crisscrossed apertures with a central straight aperture, but showing one of the larger crisscrossing apertures as being curved.

FIG. 17B is similar to FIG. 17A; however, the drawing shows one the crisscrossing apertures, 3, as being curved. The curved aspect of the aperture is probably the best manner to actually build crisscrossing apertures within the anchor and the curve will serve to better guide instruments through the enclosed conduit (the conduit that passes through the crisscrossing apertures). FIG. 17B really serves to illustrate the best mode to make the crisscrossing apertures; although, the actual shape (curved or straight) will be set by the style of instrument to pass through the conduit/aperture pair.

As shown in FIG. 16, it is possible to incorporate rotatable seals 25 within the apertures 2 of the body anchor 1, which would allow the conduits 15, 16 to rotate with respect to the body anchor 1 and to themselves. This would then aid in vectoring surgical instruments for triangulation.

Figure 2:
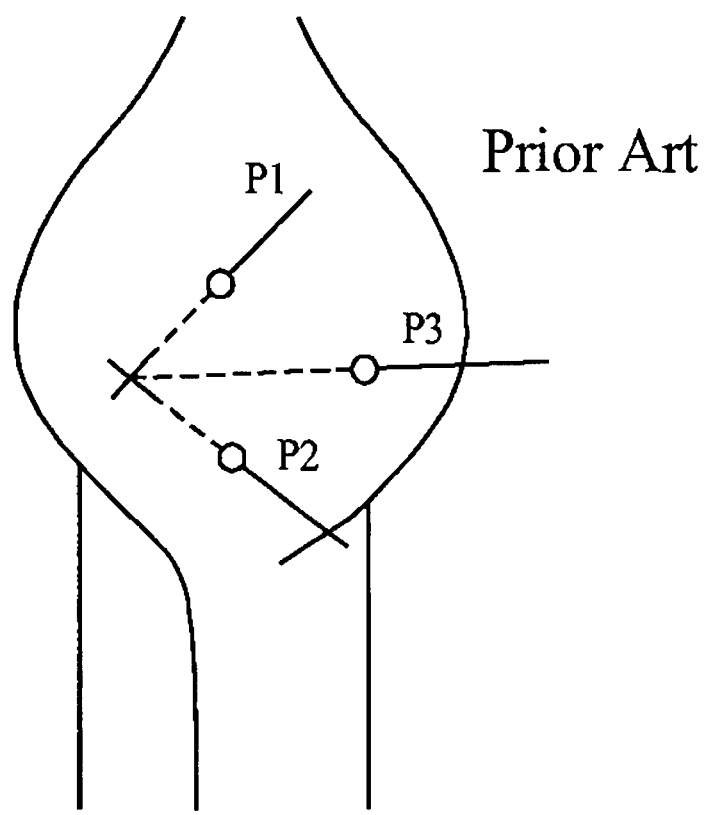

FIGS. 1 and 2 shows the current art using a plurality of canula or instruments. Port 1 (P1 in FIGS. 1 and 2) is equivalent to the single port (P1) in FIGS. 3 and 4. The crisscrossed conduits (TAU) of the instant invention serve the same function as ports 2 and 3 (P2 and P3) in FIGS. 1 and 2—the prior art. One of the conduits serves to allow the optics to enter the surgical area while the other conduit serves to allow for additional instruments. Note how the field of view gives a three dimensional effect (so that distance can be judged by the surgeon) is obtained with the single port using the instant invention as compared to three (or more) ports of the prior art.

FIGS. 3 and 4 show clearly how the flexible channel (flex-scope) serves the same function as the canula of ports 2 and 3. Some surgical procedures only need two ports (for example P1 and P2) thus; FIG. 16 shows a direct replacement for this procedure. On the other hand, most procedures required three points of access as shown in FIGS. 1 and 2 (for example P1, P2 and P3) thus; FIG. 16 shows a direct replacement for this procedure. The bendable flex-scope holds the optics and provides one or more additional channels for instruments. It should be noted that the second instrument may also be bendable.

It should be noted that FIGS. 1 through 4 imply a laparoscopic appendix operation. Referring now to FIG. 4 and single port P1, if something goes wrong during the laparoscopic procedure (e.g. a burst appendix) and the normal procedure has to be performed, port P1 need only be extended for the surgeon the "fall-back" to the standard appendectomy.

To use the device, the surgeon would carefully choose the position of the single port opening. The choice is relatively simply. The single port opening must allow for proper cross-over of the instruments so that a three-dimensional view of the surgical area of interest is obtained. The surgeon makes the incision using standard techniques inserts the instant device, sutures the device in place and runs the flex-scope and required instruments through the appropriate conduit in the device. Standard and proven techniques are then used to perform the surgery. Closing is standard.

FIGS. 18A and 18B show how surgical instruments when passed through the conduit which are crisscrossed within the body anchor will automatically align along a straight line within the body. This means that the surgeon, as the instruments are inserted, mentally knows how the instruments are aligned and the triangulation required for depth perception is guaranteed. FIGS. 19A, 19B, 20A, and 20B show how the required guaranteed triangulation cannot be obtained. Thus a single body flange, which can be extremely small compared with the current art, can be used to guarantee the required triangulation for depth perception.

What has been disclosed is an apparatus and method for an improvement to minimally invasive (laparoscopic) surgery. The technique shown uses one body flange in a single body opening; however, a second body opening is not outside the scope of the method and apparatus. The preferred mode using crisscrossed conduits has been described; however, parallel conduits and even a combination of crisscrossed and parallel conduits are envisioned. The conduits themselves which pass through the apertures of the body plug guarantee triangulation for depth perception within the body flange.

We claim:

1. A multiple access body uniport for performing minimally invasive laparoscopic surgery on a body, comprising:
   a one-piece body anchor defined by a longitudinal length and an uppermost surface and a lowermost surface, wherein:
   at least two surgical instrument passageways are located through said one-piece body anchor and terminate at an entrance aperture on said uppermost surface of said one-piece body anchor and at an exit aperture on said lowermost surface of said one-piece body anchor; and said at least two surgical instrument passageways criss-cross each other within said body anchor.

2. The one-piece body anchor of claim 1 wherein an outer perimeter of said one-piece body anchor is in direct contact with tissue of said body incised for said minimally invasive laparoscopic surgery.

3. The one-piece body anchor of claim 1 wherein at least one of said at least two surgical instrument passageways are curved.

4. The one-piece body anchor of claim 1 further including at least a third surgical instrument passageway that extends through said one-piece body anchor from said uppermost surface to said lowermost surface.

5. The one-piece body anchor of claim 4 wherein said at least third surgical instrument passageway crosses both of said at least two surgical passageways within said of body anchor.

6. The one-piece body anchor of claim 1 further including an access conduit connected to and extending outwardly from said uppermost surface, said access conduit coupled to and providing surgical instrument access to one of said at least two surgical instrument passageways.

7. The one-piece body anchor of claim 6 wherein said access conduit is a first access conduit and said one-piece body anchor further includes a second access conduit connected to and extending outwardly from said uppeimost surface, said second access conduit being coupled to and providing surgical instrument access to a second of said at least two surgical instrument passageways.

8. The one-piece body anchor of claim 7 wherein at least one of said first and second access conduits are curved.

9. The one-piece body anchor of claim 7 wherein both of said first and second access conduits are curved.

10. The one-piece body anchor of claim 1 wherein each of said at least two surgical instrument passageways includes an inflation gas seal.

11. The one-piece body anchor of claim 10 wherein said inflation gas seal is a rotatable inflation gas seal that is configured to allow rotation of a surgical instrument received within said at least two surgical instrument passageways.

12. The one-piece body anchor of claim 7 further comprising a suture attachment structure located on one or both of said first and second access conduits.

13. The one-piece body anchor of claim 12 wherein a suture is attached to said suture attachment structure and said tissue.

14. The one-piece body anchor of claim 13 wherein said suture passes through a notch on a perimeter of said uppermost surface of said one-piece body anchor.

* * * * *